United States Patent [19]
Nikolic et al.

[11] Patent Number: 6,020,508
[45] Date of Patent: Feb. 1, 2000

[54] RADIATION- OR THERMALLY-INITIATED CATIONICALLY-CURABLE EPOXIDE COMPOUNDS AND COMPOSITIONS MADE FROM THOSE COMPOUNDS

[75] Inventors: Nikola A. Nikolic, Three Bridges; Rose Ann Schultz, Princeton, both of N.J.

[73] Assignee: National Starch and Chemical Investment Holding Corporation, Wilmington, Del.

[21] Appl. No.: 08/857,668

[22] Filed: May 16, 1997

[51] Int. Cl.⁷ .................... C07D 303/00; C07D 303/12
[52] U.S. Cl. ............................ 549/512; 549/554
[58] Field of Search .................... 549/554, 512

[56] References Cited

U.S. PATENT DOCUMENTS

| | | | |
|---|---|---|---|
| 3,455,967 | 7/1969 | Hatch | 260/348 |
| 3,506,612 | 4/1970 | Neville | 260/47 |
| 4,096,154 | 6/1978 | Rempfler et al. | 260/327 R |
| 4,256,828 | 3/1981 | Smith | 430/280 |
| 4,731,428 | 3/1988 | Waterman | 528/69 |
| 5,086,189 | 2/1992 | Lecloux et al. | 549/531 |
| 5,118,822 | 6/1992 | Shum et al. | 549/529 |

FOREIGN PATENT DOCUMENTS

| | | | |
|---|---|---|---|
| 0 763 555 A2 | 3/1997 | European Pat. Off. | C08G 65/26 |
| WO 95/21207 | 8/1995 | WIPO | C08G 59/22 |
| WO 96/13538 | 5/1996 | WIPO | C08G 59/68 |
| WO 97/21229 | 6/1997 | WIPO | H01B 1/22 |

OTHER PUBLICATIONS

Lau et al, Chemical Abstract vol. 105 No. 172030, "Diphenylhexafluoropropane Derivatives" 1986.

Favretto et al, Chemical Abstract vol. 126, No. 305 358, "The Mass Spectrometric Behavior of Some Halogen–Containing Epoxyethers" 1997.

J.J. Murphy, R. G. Jones, G. Cordina, "Electron beam resists based on oxirane functionalised polystyrenes", Microelectronic Engineering 35 (1997) 121–124.

Richard G. Jones, Gerard P–G Cordina, Julian J. Murphy, "Radiation chemistry and the lithographic performance of chemical amplification resists formulated from poly(4–epoxystyrene–stat–styrene) and a photoacid generator", J. Mater. Chem., 1997, 7(3), 421–427.

CA Selects: Photocatalysts, Issue 4, 1996; Abstract 124:57986j "Photocurable compositions with short curing time for three–dimensional molding, and photocuring accelerating method".

CA Selects: Photocatalysts, Issue 4, 1996; Abstract 124:57988m "Photosensitive polyamide–based polymer compositions with good storage stability, sensitivity, and image formation".

J. V. Crivello, "Latest Developments in the Chemistry of Onium Salts", Department of Chemistry, Rensselaer Polytechnic Institute, Troy, NY, Chapter 8, pp. 435–471.

Nigel P. Hacker, "New Reactions of Cationic Photoinitiators", IBM Research Division, San Jose, CA, Chapter 9, pp. 473–504.

Abdul–Rasoul, et al., "Photochemical and thermal cationic polymerizations promoted by free radical initiators", Polymer, 1978, vol. 19, Oct., pp. 1219–1223.

J. V. Crivello et al., "Diaryliodonium Salts as Thermal Initiators of Cationic Polymerization", Journal of Polymer Science: PolymerChemistry Edition, vol. 21, 97–109 (1983).

J. V. Crivello, Adv. Poly. Sci., 1984, 62, 1–48, pp. 1–48.

Paul F. Corey et al., "Buffered Potassium Peroxymonosulfate–Acetone Epoxidaiton of $\alpha,\beta$–Unsaturated Acids", J. Org. Chem. 1986, 51, 1925–1926.

J. Wells Carter et al., "Formulation Variables Affecting Extractables in Cationic, UV–Cured, Epoxide Coatings", Water–Borne, Higher–Solids and Powder Coatings Symposium, Feb. 26–28, 1992, New Orleans, LA, pp. 421–430.

D. Billy Yang et al., "Inorganic and Organometallic Photoinitiators", *Radiation Curing; Science and Technology*, edited by S. Peter Papas. Plenum Press, NY, 1992.

James V. Crivello et al., "Studies of Synthesis and Cationic Photopolymerization of Three Isomeric Monoterpene Diepoxides", Journal of Polymer Science: Part A: Polymer Chemistry, vol. 33, 1881–1890 (1995).

C. Priou et al., "Cationic Photopolymerization of Epoxy Modified Silicones for Application to Silicone Release papers: A New Photoinitiator", Journal of Coatings Technology, vol. 67, No. 851, Dec. 1995.

March, J. Adv. Org. Chem., 4th Ed., John Wiley & Sons, NY, 1993, pp. 974–975.

James V. Crivello et al., "Novel Epoxynorbornane Monomers. 1. Synthesis and Characterization", *Macromolecules*, vol. 29, No. 1, 1996, pp. 433–438.

James V. Crivello et al., "Novel Epoxynorbornane Monomers. 2. Cationic Photopolymerization", *Macromolecules*, vol. 29, No. 1, 1996, pp. 439–4445.

Ivo Reetz et al., "Thermally induced radical promoted cationic polymerization using a novel N–allyloxypyridinium salt", Macromol. Chem. Phys. 198, pp. 19–28 (1997).

*Primary Examiner*—John Kight
*Assistant Examiner*—Raymond Covington
*Attorney, Agent, or Firm*—Jane E. Gennaro

[57] ABSTRACT

Radiation- or thermally-initiated cationically-curable compounds based on styrene oxide moieties are linked to organic molecules, oligomers or polymers.

3 Claims, No Drawings

RADIATION- OR THERMALLY-INITIATED CATIONICALLY-CURABLE EPOXIDE COMPOUNDS AND COMPOSITIONS MADE FROM THOSE COMPOUNDS

FIELD OF THE INVENTION

This invention relates to radiation- or thermally-initiated, cationically-curable epoxide compounds, and adhesives or coatings comprising those epoxide compounds.

BACKGROUND OF THE INVENTION

Electron-beam and UV-cured adhesives are currently the most rapidly growing segments of the radiation-cured polymer market. Of particular commercial importance are UV-curable epoxide adhesive formulations, which typically consist of three principle components: i) cationic photoinitiators, ii) alcohols or polyols, and iii) epoxide monomers.

The photoinitiators are chemically-inert compounds that liberate acidic species upon exposure to actinic radiation. These acidic species then catalyze the crosslinking of the epoxide monomers. Typical photoinitiators include diaryliodonium, triarylsulfonium and ferrocenium salts.

Alternatively, it is possible to thermally initiate cure through the use of onium or pyridinium salts that are known to afford cationic species capable of initiating cationic cure upon heating. For example, it is known that N-benzylpyridinium and related quaternary ammonium salts afford acidic species under thermolysis conditions (Lee, S. B.; Takata, T.; Endo, T., *Macromolecules,* 1991, 24, 2689–2693). It is also known that diaryliodonium salts thermally decompose in the presence of catalytic amounts of copper compounds (Crivello, J. V.; Lockhart, R. T. P.; Lee, J. L., *J. Polym. Sci., Polym. Chem. Ed.* 1983, 21, 97), and that these diaryliodonium salts can be converted to acidic species via decomposition of benzpinacol (Abdul-Rasoul, F. A. M.; Ledwith, A.; Yagci, Y. *Polymer,* 1978, 19,1219–1223), or peroxides (Crivello, J. V.; Lam, J. H. W. *Polym. Photochem.* 1982, 2, 219). A recent report indicates that N-allyloxypyridinium salts can be thermally converted to acidic species in the presence of 2,2'-azobutyronitrile or benzoyl peroxide (Reetz, I.; Bacak, V.; Yagci, Y. Macromol. Chem. Phys. 1997, 98, 19–28). Any of these routes will liberate cationic species capable of effecting the ring-opening polymerization of the styrene oxides.

The alcohols or polyols act as a source of active protons, facilitating the conversion of the photo- or thermal-initiator to an acidic or cationic species, and can provide needed flexibility and impact resistance to the formulation through copolymerization with the epoxides.

The epoxide monomers used in these prior art formulations are mainly cycloaliphatic epoxides, although glycidyl esters, glycidyl ethers and epoxidized alpha-olefins also have been used. The cycloaliphatic epoxides are the preferred compounds because they are more reactive than epoxides of straight chain aliphatics under cationic cure conditions. It has been surmised that this greater reactivity is the result of two structural features: cleavage of either C—O bond leads to formation of a relatively stable secondary carbocation; and cleavage of a C—O bond releases the ring-strain associated with the bicyclic ring fusion. The most common epoxide resin in UV-curable formulations is a bis-cyclohexene oxide (available from Union Carbide, product ERL-4221) connected by an ester group. This bis-cyclohexene oxide possesses sufficient reactivity to provide good crosslinking at ambient temperature. Moreover, the ester group is the only other functionality present and it is transparent to UV-radiation. However, there are drawbacks to this monomer. The bis-epoxide is an inherently non-flexible material and consequently produces a brittle crosslinked network. Such brittle materials are susceptible to mechanical stresses in manufacturing operations or end use applications. To counteract this, the epoxide can be co-reacted with one or more flexible diols in order to provide needed flexibility. However, the cycloaliphatic epoxides are not compatible with a particularly broad range of diols, which consequently limits the range of properties that may ultimately be achieved.

Although Crivello, et al. (*Radiation Curing in Polymer Science and Technology,* Vol. 2, J. P. Fouassier and J. F. Rabek (Eds.), Elsevier Applied Science, New York, 1993, pp 435–472; *Macromolecules,* 1996, 29, 433–438 and 439–445; and *J. Polym. Sci., Polym. Chem.* 1995, 33,1881–1890) have reported several epoxide structures (e.g., norbornene oxides and limonene oxides) that reputedly overcome some of the drawbacks of traditional cyclohexene oxides, there is a need for new compounds that are cationically curable and that avoid the problems of the cycloaliphatic epoxides.

DESCRIPTION OF THE INVENTION

This invention comprises radiation- or thermally-initiated cationically-curable compounds having the following structures:

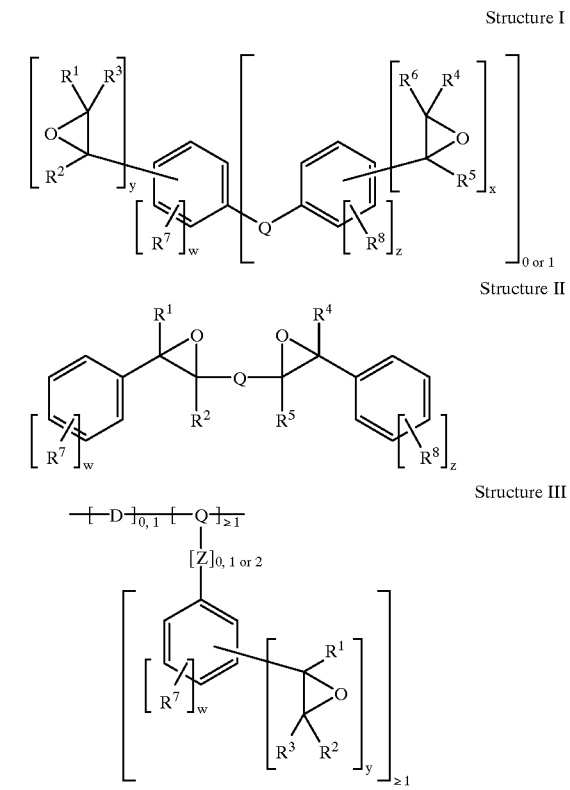

in which D, Q and Z independently represent aliphatic, alicyclic or aromatic groups, which may contain heteroatoms, characterized in that they do not hinder the cationic polymerization of the epoxy functionality either through steric interaction or through the action of a Lewis base; and $R^1$ through $R^8$ independently represent hydrogen, or aliphatic, alicyclic or aromatic groups, which may contain heteroatoms, characterized in that the groups do not hinder the cationic polymerization of the epoxy functionality either through steric interaction or through action as a Lewis base; y is an integer 1–5, w is an integer 0–4, provided that y+w≦5; and x is an integer 1–5, z is an integer 0–4, provided that x+z≦5.

For structure II, no stereochemistry is implied, and all stereoisomers are deemed included by that structure.

The notable feature of these compounds is that the styrene oxide moiety, which can be cured cationically, can be linked to selected molecular, oligomeric, or polymeric entities.

Therefore, it will be understood that the R, Q and Z substituents may be any desired organic groups designed to give predetermined properties in those end use applications where a cationic cure is desired. For example, but not by way of limitation, these substituents may be a small organic group, such as a lower alkyl hydrocarbon or one unit of a siloxane; or may be oligomeric or polymeric in size and nature and contain heteroatoms, such as oxygen, nitrogen, sulfur and silicon, as is found in polyethers, polyesters, polyurethanes, and polysiloxanes. It can be understood from the structures that Q and Z differ from the R substituents in that they may be the same organic group or may be different; for example in Structure III, Q may be a polysiloxane and Z may be an ester linkage.

As will be understood, organic moieties can be selected for specific chemical and physical properties, such as hydrophilic or hydrophobic properties, toughness, strength or flexibility. By way of example, it is known that flexibility can be obtained in a compound by the absence of ring structures, low levels of crosslinking, and free rotation about polymeric bonds. Carbon-carbon double bonds adjacent to carbon-carbon single bonds, and ester and ether groups enhance free rotation. As another example, it is also known that siloxane moieties impart hydrophobicity and flexibility. Thus, by judicious choice, the compositions of Q and Z can be designed to meet the required properties of any end use applications where a cationic cure is desired.

Examples of representative styrene oxide moieties, but not intended as a limitation, are those derived from cinnamyl alcohol, isoeugenol, or vanillin, as depicted here:

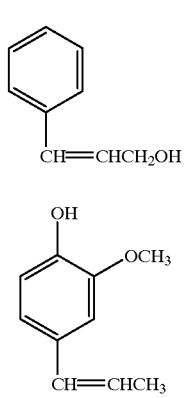

cinnamyl alcohol isoeugenol

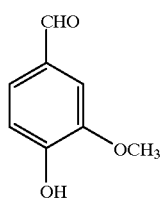

vanillin

There are many and varied synthetic routes known and used by those skilled in the art to the epoxides of this invention. An exemplary potential synthetic route beginning with cinnamyl alcohol or isoeugenol entails the reaction of the hydroxyl functionality with an alkyl dibromide or an aliphatic bis-epoxide using standard reaction conditions as are known in the art, and the subsequent epoxidation of the olefinic functionality.

The epoxidation may be performed by any suitable method known in the art. One preferred method is conducted through a potassium monopersulfate/acetone oxidation of the olefinic portion of the corresponding styrene. The olefinic compound is suspended in a mixture of acetone and water, and buffered with sodium bicarbonate, which serves to prevent decomposition of the resultant oxides. This suspension is then treated with an excess of the oxidant, provided as an aqueous solution of monopersulfate compound ($2KHSO_5 \cdot KHSO_4 \cdot K_2SO_4$) (Oxone®, a product of DuPont). The recovered solution is partitioned with ethyl acetate, toluene, methylene chloride, or other suitable solvent. Workup consists of washing the organic layer with water followed by drying with a non-acidic drying agent (e.g., anhydrous sodium bicarbonate). Filtering this mixture, followed by removal of organic solvent in vacuo, affords the desired epoxide.

A synthetic route beginning with vanillin also involves the reaction of the hydroxyl functionality with an alkyl dibromide or an aliphatic bis-epoxide, and subsequent reaction of the aldehyde functionality with a sulfur ylide under known reaction conditions to provide the epoxide. (See, March, J. in *Advanced Organic Chemistry*, 4th Ed., John Wiley & Sons, N.Y., 1993, pp 974–975.)

These styrene oxides are eminently suitable for use in cationically-curable compositions for several reasons. They are extremely reactive crosslinking agents, curing at room temperature, and they polymerize faster than analogous compositions containing cycloaliphatic epoxides. This faster cure speed implies faster processing speeds for end users, and the higher reactivity translates into formulations that require decreased amounts of monomer while delivering identical rates and extents of cure.

Thus, this invention further comprises radiation- or thermally-initiated cationically-curable compositions, such as, adhesives, or coatings or encapsulants, comprising a compound containing at least one styrene oxide group as described herein, a cationic photoinitiator or thermal initiator, and optionally one or more alcohols or polyols.

Suitable photoinitiators include those diaryliodonium, triarylsulfonium and ferrocenium salts that are known to initiate cationic cure. Suitable thermal initiators are onium or pyridinium salts that are known to afford cationic species capable of initiating cationic cure upon heating. For example, N-benzylpyridinium and related quaternary ammonium salts, diaryliodonium salts that thermally decompose in the presence of catalytic amounts of copper compounds, N-allyloxypyridinium salts that can be thermally converted to cationic species in the presence of 2,2'-azobutyronitrile or benzoyl peroxide. The initiators will be present in any effective amount to initiate the cationic cure process, and customarily will be present in amounts of 0.1 to 10% by weight of the composition.

The preferred hydroxyl-containing compounds are diols, such as, polycaprolactone diols (e.g. the diol sold under the tradename Tone 0201, a product of Union Carbide); polyester diols (e.g. the diol sold under the tradename Rucoflex S-107-210, a product of Ruco Polymer Corporation); bisphenol A based polyether diols (e.g. the diol sold under the tradename Syn Fac 8031, a product of Milliken Chemicals); aliphatic diols (e.g. the diol sold under the tradename MP-diol, a product of Arco Chemical Company); aromatic polyester diols (e.g. the diol sold under the tradename Stepanpol, a product of Stepan Company). When used, the alcohol or polyol commonly will be present in a molar ratio of the hydroxyl functionality to the epoxide functionality in a range of 1:10 to 10:1, although any effective ratio can be used to obtain the desired end use properties.

In some end use adhesive or coating applications, the compositions may contain inert or electrically or thermally conductive fillers. The weight percentages and choice of filler for various end use applications will be known to those skilled in the art. Examples of such fillers are carbon, silica, alumina, silver, copper, gold, nickel, aluminum nitride, boron nitride, and silicon carbide. Typically, such fillers will be present in amounts ranging up to about 95% by weight of the composition.

These compositions have advantages over prior art formulations containing cycloaliphatic epoxides. For cycloaliphatic epoxides, such as those derived from cyclohexene oxide, and typical photoinitiators, it has been surmised that moisture may slow the cure rate by reacting with the superacid initiating species (e.g., $HSbF_6$, which would be derived from $Ar_3S^+SbF_6^-$, a typical photoinitiator) to form a hydronium ion and a counterion. The hydronium ion is not sufficiently acidic to react with the cycloalipatic epoxide and continue the crosslinking.

In contrast, the epoxy functionality of the styrene oxide monomers is more easily ring-opened to form the benzylic carbocation in the presence of either a superacid or a hydronium ion, and consequently the polymerization is continued and not terminated by the reaction of the initiating species with moisture. Furthermore, the enhanced reactivity and longer lifetime of the benzylic carbocation permit cure to continue even after exposure to the actinic radiation is ceased, and may allow for curing in regions that were not directly exposed to the actinic radiation, so-called dark curing.

In addition, these monomers contain an aromatic chromophore that absorbs actinic energy at wavelengths other than the wavelengths that activate the photoinitiators. This absoprtion promotes the monomers to an excited state and results in increased reactivity. This aromatic benefit is not possible in cycloaliphatic epoxides, which do not possess chromophore substituents.

The enhanced reactivity and longer lifetime of the styrene oxide moieties make them an ideal group for addition onto any molecular, oligomeric or polymeric support where cationic cure is desired.

The following are examples of the synthesis of representative compounds of this invention and of the reactivity of the styrene oxide moieties.

EXAMPLE 1

Preparation of a Bis-Styrene Oxide Precursor

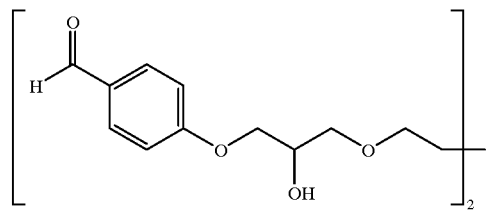

A four necked round-bottomed flask was charged with butanediol diglycidyl ether (12.52 g, 62.0 mmol) (Aratronic 5320, Product of Ciba-Geigy), 4-hydroxybenzaldehyde (7.76 g, 127 mmol), and tetramethylammonium chloride (0.28 g, 2.5 mmol). The resulting mixture was lowered into a pre-heated oil bath at 85° C. The reaction mixture became a brown, transparent solution. The temperature was increased to 120° C. and held at this temperature for 3.5 hours. After this interval, the reaction mixture was cooled and dichloromethane (200 mL) was added. The resulting solution was transferred to a separatory funnel and washed with 2N KOH (2×20 mL), and brine (30 mL). The organics were dried over anhydrous sodium bicarbonate, filtered, and the solvents removed in vacuo to afford the desired bis-aldehyde.

EXAMPLE 2

Sulfur Ylide (Phase Transfer) Approach to the Epoxide

A 500 mL 4-necked flask was charged with the bis-aldehyde (5.0 g, 11.2 mmol) from Example 1, and dichloromethane (35 mL). To the resulting solution was added trimethylsulfonium iodide (9.15 g, 44.8 mmol), water (14 mL) and benzyltrimethylammonium chloride (0.31 g, 1.4 mmol). The resulting mixture was stirred vigorously while 50% NaOH (35 mL) was added dropwise of a period of 2 hours. Then the mixture was stirred at ambient temperature for 24 hours. After this interval, water (20 mL) was slowly added, and the layers were partitioned. The organics were partitioned and the organic phase was washed with saturated sodium bicarbonate (2×50 mL). The organics were dried over anhydrous sodium bicarbonate, filtered, and the solvents removed in vacuo to afford a 50:50 mixture of the desired bis-epoxide and the starting bis-aldehyde.

The mixture of the bis-epoxide and the starting bis-aldehyde was reintroduced to the reaction flask and the procedure repeated twice more. The desired bis-epoxide was obtained in greater than 90% purity (1.01 g, 2.12 mmol, 19%).

EXAMPLE 3

Sulfur Ylide (Potassium t-Butoxide) Approach to the Bis-Epoxide

A 500 mL 3-necked bound-bottomed flask was charged with potassium t-butoxide (14.86 g, 121.7 mmol) and tetrahydrofuran (100 mL). The resulting suspension was cooled to 0° C., and trimethylsulfonium iodide (18.45 g, 90.3 mmol) was added in small portions. When addition was complete, the resulting suspension was allowed to stir at 0° C. for 1 hour. After this interval, a solution of the bis-aldehyde from Example 1 in tetrahydrofuran (13.45 g, 30.1 mmol) (110 mL) was added dropwise over a period of 20 minutes. The suspension was stirred at 0° C. for 1 hour, and then allowed to warm to ambient temperature for 2 hours.

After this interval, the reaction was quenched by dropwise addition of water (60 mL), followed by diethyl ether (250 mL). The layers were partitioned, and the aqueous phase was extracted with diethyl ether (3×125 mL). The organics were combined, washed with saturated sodium bicarbonate (2×50 mL), and dried over anhydrous sodium bicarbonate. The organics were filtered, and the solvents removed in vacuo to afford the desired bis-epoxide (19.17 g, 64% yield).

EXAMPLE 4

A bis-olefin was derived from isoeugenol (using an alkyl bromide as described above) to give the following compound

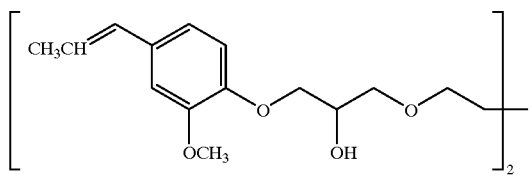

This compound can be oxidized by any suitable method known in the art and will afford the corresponding bis-styrene oxide.

EXAMPLE 5

UV Formulations

In order to demonstrate suitability for UV-curing, an alpha-methylstyrene oxide monomer was formulated into adhesive compositions with various diols and, as the photoinitiator, 1% by weight of a 50% by weight solution of an arylsulfonium salt in propylene carbonate, sold under the tradename UVI-6974 by Union Carbide. These compositions were compared to control formulations containing a cycloaliphatic epoxide obtained from Union Carbide, as product ERL-4221, which has the structure:

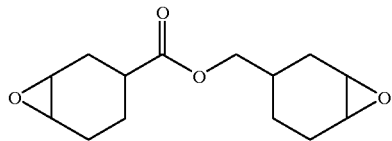

A sample in the range of 1.5 to 3.0 mg for each composition was exposed to UV radiation and the rate of cure followed by a DPA-7 Perkin-Elmer Photo-Differential Scanning Calorimeter (P-DSC). Each sample was equilibrated to constant temperature (25° C.) on the Calorimeter for one minute and then exposed to irradiation for a total of four minutes using a 100 Watt Mercury short arc lamp. The resultant traces showed an exotherm represented as a sharp or broad peak. The diol used in the compositions, the molar ratio of epoxy to diol, and the DSC results are set out in Table 1 for the inventive styrene epoxy, and in Table 2 for the cycloaliphatic epoxy. In the Tables, $T_{max}$ is the time it took to reach the peak maximum exotherm in seconds, and $\Delta H$ is the exotherm of the reaction in kJoules per mole of epoxy, measured as the area over the curve from the four minute baseline back to the onset of exotherm.

The time the reaction takes to reach $T_{max}$ is a direct indication of the speed of the reaction; thus, the shorter the time (i.e., the sharper the peak), the faster the cure reaction for the epoxy, which is a desirable property for these adhesive compositions. In the following tables, the peaks are designated either sharp or broad; for purposes herein, if more than half the exotherm occurred in the first 30 seconds, the peak was defined as sharp, and conversely, if less than half the exotherm occurred in the first 30 seconds, the peak was defined as broad.

The $\Delta H$ values are a direct indication of the degree of epoxy ring opening, with the more negative numbers reflecting the higher degree of conversion of the epoxy.

The results indicate that the styrene compositions cure more quickly and more fully than cycloaliphatics, and that they are more compatible with a broader range of diols and at varying molar ratios than the cycloaliphatics. Referring to the data in Tables 1 and 2, it can be seen that the rates of cure ($T_{max}$) extend from 2.94 seconds to 6.12 seconds for the styrene epoxy, and from 4.62 seconds to 42.66 seconds for the cycloaliphatic epoxy, and that the extents of cure range from −79.1 kJ to −56.4 kJ for the styrene epoxy, and from −79.4 to −10.0 kJ for the cycloaliphatic epoxy. These ranges show that the rates of cure and extents of cure for the formulations containing the styrene epoxy were less affected by the choice of diol and the ratio of epoxide to diol than were the formulations containing the cycloaliphatic epoxy.

The diols that were used in the formulations are designated in the Tables by their tradenames. The diol sold under the tradename Tone 0201 is a product of Union Carbide and is a polycaprolactone diol. The diol sold under the tradename Rucoflex S-107-210 is a product of Ruco Polymer Corporation and is a polyester diol. The diol sold under the tradename Syn Fac 8031 is a product of Milliken Chemicals and is a bisphenol A based polyether diol. The diol sold under the tradename MP-diol is a product of Arco Chemical Company and is an aliphatic diol. The diol sold under the tradename Stepanpol is a product of Stepan Company and is an aromatic polyester diol.

TABLE 1

DSC Data for Styrene Oxide Monomer

| DIOL | Molar Ratio Epoxy: Diol | $T_{max}$** seconds | $\Delta H$ kJ/mole epoxide |
|---|---|---|---|
| none |  | 3.84 | −57.8 |
| Rucoflex 107 | 1:1 | 4.32 | −84.1 |
| Rucoflex 107 | 3:1 | 4.20 | −79.1 |
| SynFax 8031 | 1:1 | 4.74 | −71.8 |
| SynFac 8031 | 3:1 | 3.57 | −65.5 |
| Stepanol PS–4002 | 1:1 | 6.12 | −76.0 |
| Stepanol PS–4002 | 3:1 | 4.83 | −62.6 |
| MP–diol* | 1:1 | 4.35 | −77.4 |
| MP–diol* | 3:1 | 2.94 | −58.2 |
| Tone 0201 | 1:1 | 3.57 | −73.4 |
| Tone 0201 | 3:1 | 3.96 | −56.4 |
| Tone 0201 | 1:3 | 4.59 | −75.9 |

Notes on Table 1: *Insoluble in formulation. **All peaks are sharp.

TABLE 2

DSC Data for Comparative Epoxy ERL-4221

| DIOL | Molar Ratio Epoxy:Diol | $T_{max}$ seconds | $\Delta H$ kJ/mole epoxide |
|---|---|---|---|
| none | — | 4.62 sharp | −10.0 |
| Rucoflex 107 | 1:1 | 6.81 sharp | −68.9 |
| Rucoflex 107 | 3:1 | 2.10 sharp | −42.9 |
| SynFac 8031 | 1:1 | 13.47 broad | −67.8 |
| SynFac 8031 | 3:1 | 13.17 broad | −39.7 |
| Stepanol PS–4002 | 1:1 | 17.10 broad | −79.4 |

TABLE 2-continued

DSC Data for Comparative Epoxy ERL-4221

| DIOL | Molar Ratio Epoxy:Diol | $T_{max}$ seconds | ΔH kJ/mole epoxide |
|---|---|---|---|
| Stepanol PS-4002 | 3:1 | 5.34 sharp | −14.3 |
| MP-diol | 1:1 | 21.20 broad | −78.4 |
| MP-diol | 3:1 | 6.39 sharp | −49.0 |
| Tone 0201 | 1:1 | 9.21 broad | −62.0 |
| Tone 0201 | 3:1 | 6.00 sharp | −30.3 |
| Tone 0201 | 1:3 | 42.66 broad | −44.0 |

EXAMPLE 6

To show the curing capability of selected styrene oxides with substituted epoxy and aromatic rings, various styrene oxides were formulated with a photoinitiator and a diol and subjected to Photo-Differential Scanning Calorimetric analysis. The specific formulation of styrene oxide, diol, molar ratio of epoxide to hydroxyl functionality, $T_{max}$, and the kJ per mole of epoxy are set out in the following Table 3:

TABLE 3

| MONOMER | DIOL | Molar ratio Epoxy:Diol | $T_{MAX}$ | ΔH kJ/mole Epoxide |
|---|---|---|---|---|
| 1. alpha-methyl styrene bis epoxy | — | — | 3.84 | −57.8 |
| 2. alpha methyl styrene epoxy | — | — | 3.60 | −53.3 |
| 3. alpha methyl styrene epoxy | MP-diol* | 1:1 | 3.12 | −80.9 |
| 4. alpha methyl styrene epoxy | MP-diol* | 3:1 | 2.88 | −56.4 |
| 5. alpha methyl styrene bis epoxy | Tone polyol | 1:1 | 3.57 | −72.8 |
| 6. alpha methyl styrene epoxy | Tone polyol | 1:1 | 3.78 | −76.5 |
| 7. alpha methyl styrene epoxy | Tone polyol | 3:1 | 3.30 | −66.7 |
| 8. beta-methyl styrene epoxy | — | — | 4.62 | −85.4 |
| 9. beta-methyl styrene epoxy | MP-diol* | 1:1 | 5.28 | −102.6 |
| 10. beta-methyl styrene epoxy | MP-diol* | 3:1 | 4.98 | −75.7 |
| 11. beta-methyl styrene epoxy | Tone polyol | 1:1 | 8.28 | −80.5 |
| 12. beta-methy styrene epoxy | Tone polyol | 3:1 | 6.24 | −54.5 |
| 13. cinnamyl acetate epoxy | — | — | 0 | 0 |
| 14. cinnamyl acetate epoxy | MP-diol* | 1:1 | 8.76 | −27.5 |
| 15. cinnamyl acetate epoxy | MP-diol* | 3:1 | 8.58 | −16.1 |
| 16. cinnamyl acetate epoxy | Tone polyol | 1:1 | 11.22 | −55.6 |
| 17. cinnamyl acetate epoxy | Tone polyol | 3:1 | 10.23 | −30.8 |
| 18. isoeugenol acetate epoxy | — | — | 23.1 | −15.7 |
| 19. isoeugenol acetate epoxy | MP-diol | 1:1 | 7.17 | −70.1 |
| 20. isoeugenol acetate epoxy | MP-diol | 3:1 | 7.50 | −67.6 |
| 21. isoeugenol acetate epoxy | Tone polyol | 1:1 | 8.76 | −75.0 |
| 22. isoeugenol acetate epoxy | Tone polyol | 3:1 | 9.39 | −65.0 |
| 23. cinnamyl methyl ether epoxy | — | — | 7.38 | −43.9 |
| 24. cinnamyl methyl ether epoxy | MP-diol* | 1:1 | 14.46 | −57.8 |
| 25. cinnamyl methyl ether epoxy | MP-diol* | 3:1 | 13.65 | −63.6 |
| 26. cinnamyl methyl ether epoxy | Tone polyol | 1:1 | 3.18 | −98.8 |
| 27. cinnamyl methy ether epoxy | Tone polyol | 3:1 | 2.40 | −82.4 |

*Insoluble in formulation

What is claimed is:

1. A radiation- or thermally-initiated cationically-curable compound having the structure:

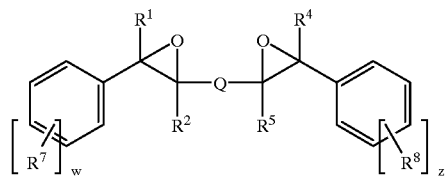

in which Q represents aliphatic, alicyclic or aromatic groups, which may contain oxygen, nitrogen, sulfur or silicon, characterized in that they do not hinder the cationic polymerization of the epoxy functionality either through steric interaction or through the action of a Lewis base; and $R^1$, $R^2$, $R^4$, $R^5$, $R^7$ and $R^8$ independently represent hydrogen, aliphatic, alicyclic or aromatic groups, which may contain heteroatoms, characterized in that they do not hinder the cationic polymerization of the epoxy functionality either through steric interaction or through the action of a Lewis base; and w and z are independently integers of 1–5.

2. An adhesive composition comprising the radiation- or thermally-initiated cationically-curable compound of claim 1 and a photo- or thermal-initiator.

3. A coating composition comprising the radiation- or thermally-initiated cationically-curable compound of claim 1 and a photo- or thermal-initiator.

* * * * *